United States Patent [19]
Revelas

[11] Patent Number: 5,968,053
[45] Date of Patent: Oct. 19, 1999

[54] METHOD AND APPARATUS FOR IMPLANTING A GRAFT IN A VESSEL OF A PATIENT

[75] Inventor: Demetrios Revelas, Gauteng, South Africa

[73] Assignee: Cardiac Assist Technologies, Inc., Pittsburgh, Pa.

[21] Appl. No.: 08/792,562

[22] Filed: Jan. 31, 1997

[51] Int. Cl.⁶ ...................................................... A61F 11/00
[52] U.S. Cl. .............................. 606/108; 606/198; 623/1; 623/12
[58] Field of Search ................................ 606/1, 108, 151, 606/191–200; 604/96–104; 623/1, 11, 12

[56] References Cited

U.S. PATENT DOCUMENTS

| | | | |
|---|---|---|---|
| 4,787,899 | 11/1988 | Lazarus | 606/108 |
| 5,207,695 | 5/1993 | Trout, III . | |
| 5,275,610 | 1/1994 | Eberbach | 606/198 |
| 5,423,851 | 6/1995 | Samuels | 606/198 |
| 5,480,423 | 1/1996 | Ravenscroft et al. . | |
| 5,617,878 | 4/1997 | Taheri | 606/198 |
| 5,702,419 | 12/1997 | Berry et al. | 606/108 |
| 5,713,907 | 2/1998 | Hogendijk et al. | 606/108 |

*Primary Examiner*—Glenn K. Dawson
*Attorney, Agent, or Firm*—Ansel M. Schwartz

[57] ABSTRACT

The present invention pertains to an apparatus for implanting a graft into a vessel of a patient. The apparatus includes a mechanical delivery mechanism for delivering the graft to a desired location inside the vessel and then withdrawing from the vessel. The apparatus also has an anchoring mechanism for anchoring the graft to the interior surface of the vessel from the inside of the vessel. The anchoring mechanism is connected to the delivery mechanism. The present invention pertains to a method of implanting a graft in a vessel of a patient. The method includes the steps of delivering a graft to a desired location inside the vessel with a delivery mechanism. Next, there is the step of piercing the vessel from the interior of the vessel with anchors connected to the graft from inside the vessel. Then, there is the step of anchoring the anchors in the vessel to hold the graft in the vessel by changing the shape of the anchors.

21 Claims, 7 Drawing Sheets

METHOD AND APPARATUS FOR IMPLANTING A GRAFT IN A VESSEL OF A PATIENT

FIELD OF THE INVENTION

The present invention is related to the implantation of a graft in a vessel of a patient. More specifically, the present invention is related to the implantation of a graft in a vessel with anchors that remain in the vessel.

BACKGROUND OF THE INVENTION

An aneurysm is a localized dilation of the wall of a blood vessel, usually caused by atherosclerosis and hypertension, or, less frequently, by trauma, infection, or a congenital weakness in the vessel wall ["Medical, Nursing and Allied Health Dictionary", $4^{th}$ Ed., revision editor, K. N. Anderson, Publ., Mosby-Year Book, Inc., St. Louis, Mo., USA]. Currently, the vast majority of the aneurysms are repaired by the conventional open surgical technique, referred to a aneurysmectomy. However, the mortality rate associated with this procedure remains relatively high (2–15% for elective surgery and between 30–50% for emergency surgery following vascular rupture and as high as 71% for patients above 70 years of age [M. E. Clouse, "Device for Performing Endovascular Repair of Aneurysms", U.S. Pat. No. 5,211,658, May 1993]). Furthermore, a major drawback of the procedure is that due to the nature of the surgical operation, it is generally performed in medical facilities with the necessary sophisticated equipment essential for cardiovascular procedures thereby limiting accessibility.

Morbidity and mortality rates following the conventional repair of a non-ruptured abdominal aortic aneurysms (AAA) remain some of the highest in elective surgery. Although endovascular repair has the potential to reduce these figures, its main benefit would be in reducing both the tangible and intangible costs associated with this type of surgery, see Table 1.

TABLE 1

|  | Conventional | Endovascular |
| --- | --- | --- |
| Anaesthesia | General | Local |
| Invasive | Local incision | Femoral cutdown |
| Transfusion | Yes | No |
| Procedure Time | ≧6 hrs. | 30–60 min |
| Recovery Time | ≧24 hrs. | ≦6 hrs. |
| Hospital Stay | 7–10 days | ≦3 days |
| High Risk Candidates | No | Yes |
| Male Impotency from Operation | Many | None |

Endovascular repair of AAA will reduce the cost of the procedure to the patient, particularly in terms of medical expense, rehabilitation, morbidity and recovery time.

It is widely generally accepted that JC Parodi in 1990 was the first surgeon to successfully clinically demonstrate the concept of endovascular repair of AAA [S. W. Yusuf and B. R. Hopkinson. "Endovascular Repair of Aortic Aneurysm", Leading Articles, *British Journal of Surgery*, 82, pp. 289–291, 1995]. Using a balloon expandable stent designed by JC Palmaz and a thin-walled tubular Dacron (polyethylene terephthalate) graft, Parodi galvanized the surgical community and venture capital companies, such as EndoVascular Technologies (Menlo Park, Calif.) to strive to develop improved graft designs and deployment mechanisms.

It is widely accepted that the stenting technique pioneered by Parodi is only suitable where a proximal and distal cuff of at least 20 mm is available for secure stent attachment. However, most substantial aneurysms lack such a cuff, particularly in the region of the renal arteries, therefore, Dr. D. Revelas has proposed to mechanically anastomose (to surgically join two ducts, such as blood vessels, to allow flow from one to another) the endoarterially placed graft.

Despite advances in the diagnosis and treatment of patients with AAA, more than ten thousand people die in Britain every year due to sudden rupture of an aortic aneurysm [A. Berger, "Hard Graft Cuts Out Bypass Surgery", *New Scientist, Jun.* 10, 1995], correspondingly in the USA, the number of deaths is estimated to be approximately fifteen thousand [W. S. Moore, "Endovascular Grafting Technique: A Feasibility Study", Aneurysms, New Findings and Treatments, Chapter 28, Ed., J. S. T. Yao and W. H. Pearce, Publ., Appleton & Lance, Norwalk, Conn., pp. 333–340, 1994]. In addition to improved screening and diagnostic methods for AAA, endovascular repair aims to reduce this number by enabling successful surgical intervention before the onset of the current critical aneurysm size indicated for operation (±5.0 cm).

Basically, work in the field can be divided into two broad categories, namely; the delivery system and the stenting system.

Referring first to the delivery system, the pioneering work by JC Parodi was largely dependent upon conventional stent deployment using an angioplasty balloon. EndoVascular Technologies, the only company currently to hold U.S. Food and Drug Administration (FDA) approval for clinical trials, utilize a balloon deployment system [Lazarus et al., "Endovascular Grafting Apparatus, System and Method and Devices for Use with Them", U.S. Pat. No. 5,275,622, January 1994]. Theoretically, this technique of deployment is highly accurate and reproducible, however, in practice the stent can shift, rotate or separate from the balloon during the procedure. Moreover, the metallic stents can perforate the balloon either during loading, advancement or deployment of the endovascular device resulting in improper deployment. Marin et al. with their U.S. Pat. No. 5,443,477 [Marin et al., "Apparatus and Method for Deployment of Radially Expandable Stents by a Mechanical Linkage", U.S. Pat. No. 5,443,477, August, 1995] proposed an apparatus for intraluminal delivery and deployment of an expandable prosthesis, using mechanical linkage similar to that proposed by D. Revelas [D. Revelas, "An Endovascular Anastomotic Device", SA Patent Application, August 1994]. However, even with the most modern manufacturing technologies available it is highly unlikely that a working model of the Marin device can be fabricated, although the concept of mechanical deployment is superior to that of using an angioplasty balloon.

In regard to the stenting system, greater attention has been given to the stenting device by inventors than to the delivery systems. Almost every conceivable biomaterial has been proposed as a suitable stent from resorbable polymeric materials to the very latest shape memory allows.

Generally, the stents can be divided into two main groups: expandable—these stents rely on either mechanical or balloon deployment. Typical examples are the balloon deployed stainless steel/Teflon® (polytetrafluoroethylene) EVT device [Lazarus et al., "Endovascular Grafting Apparatus, System and Method and Devices for Use with Them", U.S. Pat. No. 5,275,622, January 1994] and the mechanically deployed Fischell stent [R. E. Fischell, "Stent Having a Multiplicity of Closed Circular Structures", European Patent Application EP 0 669 114 A1, August 1995].

(Fischell also acknowledged that in addition to stainless steel, tantalum and titanium, stents fabricated from shape memory alloys could be used). In addition to patents filed for metallic materials, Stack and Klopovic [R. S. Stack and Z. P. Klopovic, "Absorbable Stent", U.S. Pat. No. 5,306,286, April 1994] filed for a device fabricated from a bioresorbable polymer. The device was either balloon or mechanically deployed, once in position tissue ingrowth and encapsulation takes place (as with a Teflon® or Dacron® graft), thereafter, the stent is absorbed, reducing the likelihood of embolization. Yet another variation was proposed in 1995 by Dayton [M. P. Dayton, "Minimally Invasive Bioactivated Endoprosthesis for Vessel Repair", U.S. Pat. No. 5,449,382, September 1995] who developed a device fabricated from either a metal or polymer which is then coated with a bioactive substance, such as heparin, hirudin, antithrombogenic or antifibrosis agents, in order to establish a chemical equilibrium with the surrounding tissue. This particular device has a novel locking mechanism to inhibit collapse of the device after deployment.

self-expandable—these devices tend to be mainly variations on the theme of mechanically constricting the stent by twisting and allowing the coiled device to spring open on deployment. Normally, the materials of choice are from the family of stainless steels. Once the correct diameter wire has been decided upon, it is usually woven into a zigzag shape. Typical examples of this type of system were patented by Sung-soon [A. N. Sung-soon, "Intraluminal Stent", European Patent Application EP 0 645 125 A1, March 1995], Fontaine [A. B. Fontaine, "Vascular Stent", U.S. Pat. No. 5,314, 472, May 1994] and a prosthesis dependent upon deployment using self-expandable stents was patented by Günther et al. [R. W. Günther et al., "An Endovascular Graft Prosthesis and an Implantation Method for Such a Prosthesis", PCT Application WO 95/16406, June 1995].

More recently, alloys which undergo a reversible volume phase transformation in the temperature range −50 to 110° C. commonly termed shape memory alloys (SMA's) have been evaluated as potential stent materials. The Ni—Ti shape memory alloy favored as a stent was developed by the U.S. Naval Ordinance Laboratories and called nitinol. The shape memory effect is one of the most intriguing phenomena in materials science. Even SMA's that have undergone quite severe distortions such as winding into a coil can be easily straightened again by the application of a small amount of heat. As the material is warmed it "remembers" its initial shape and springs back. This effect has not escaped the attention of inventors and once the Ni—Ti alloys were shown to be biocompatible numerous patents were filed utilizing this phenomenon for stent deployment. One of the first patents registered which depended on the shape memory effect for deployment was filed by Clouse [M. E. Clouse, "Method and Device for Performing Endovascular Repair of Aneurysms", U.S. Pat. No. 5,211,658, May 1993] in 1993. Patented variations include woven shape memory alloys [S. S. Lam, "Expandable Stents and Method for Making Same", European Patent Application EP 0 662 307 A1, July 1995; L. Lilip et al., "Self-expandable Stent and Stent-graft and Method of Using Them", PCT Application WO 95/26695, October 1995] (as is customary in this type of patenting these patents are not exclusively related to SMA alloys but they also refer to woven devices fabricated from a broader range of biocompatible materials).

In August 1995, Mori [K. Mori, "Stent for Biliary, Urinary or Vascular System", European Patent Application EP 0 666 065 A1, August 1995] patented the use of a SMA for use in the biliary, urinary or vascular system, what is particulary elegant about this filing is that the Austenite finishing temperature ($A_f$) ranges from 41 to 43° C. which corresponds approximately with body temperature. Therefore, the stent is capable of assuming a small diameter at temperatures below $A_f$ and an expanded configuration above or equal to $A_f$.

Recently, Bruin et al. [P. Bruin et al., "Intravascular Polymeric Stent", PCT Application WO 95/26762, October 1995] have proposed using polymeric materials based on either a) amorphous, non-crystallizable polylactic acid networks, b) highly cross-linked polyurethane networks, or c) conversion products of star prepolyesters and di-isocyanate, which exhibit shape memory effects when heated above the glass transition temperature ($T_g$).

Trout [H. H. Trout, "Aortic Graft, Implantation Device, and Method for Repairing Aortic Aneurysm", U.S. Pat. No. 5,207,695, May 1994], in U.S. Pat. No. 5,207,695, discloses an aortic graft for performing an aortic anastomosis. This is achieved using a series of barbed hooks which pierce the graft and aorta wall in order to stabilize the graft. However, Trout uses a balloon catheter as the deployment mechanism which is different to the mechanical deployment device of the present invention and suffers from all the problems inherent with a balloon catheter.

1. Any balloon device is essentially concentric, particularly if associated with a stent of any known sort. The present invention in a preferred embodiment has individual arms, each of which can take up an independent position (within limits), in an eccentric vessel. No stent is present to limit lateral conformity with an eccentric vessel. The mobility of the graft material determines the conformity of the graft to the vessel wall between the stapling devices.

2. Once stapled to the vessel wall, should the vessel itself continue to dilate (as is often the case with progressive aneurysmal disease), a stapled graft promises better compliance and adherence to the vessel wall with progressive dilatation as compared to a graft held in place by a rigid stent (this theme could be expanded).

3. Stents of any form, either self-expanding or balloon deployable, require a finite length, typically 2 cm, for secure purchase. The stapled anastomosis could conceivably be positioned in as little as 0.5 cm aortic necks with accurate localization.

4. Stapled device does not apply continuous pressure to the inner wall of the host artery, a possible disadvantage of fixed and self-expanding stents which require expansion to at least the stretched diameter of the host artery.

The potential advantages of endovascular repair of AAA has been brought close to every day realization due to advances in catheter delivery systems, fabric and stent technologies, and radiologic imaging [R. M. Green and T. A. M. Chuter, "Experimental Study of Endovascular Grafting for Aortic Aneurysm", Aneurysms, New Findings and Treatments, Chapter 27, Ed., J. S. T. Yao and W. H. Pearce, Publ., Appleton & Lance, Norwalk, Conn., pp. 325–332, 1994]. However, endovascular therapies will require extensive animal testing in order to demonstrate safety, efficacy and effectiveness. The most important criteria for a model to test endovascular graft placement is anatomic correctness. Unfortunately, no such model exists. There are, however, several small and large animal models that have been used to evaluate endovascular grafting.

Mirich et al. [D. Mirich et al., "Percutaneously Placed Endovascular Grafts for Aortic Aneurysms: Feasibility Study", *Radiology*, Vol. 170, (3PT2), pp. 1033–7, 1988] in 1988 reported on the use of six mongrel dogs with experimentally induced aortic aneurysms. Generally, the results obtained were favorable with only one dog being lost due to occlusion of both renal arteries due to thrombus formation in the vicinity of the incorrectly deployed distal grafts. Chuter [T. A. M. Chuter et al., "Endovascular Repair of Aortic Aneurysms: Straight and Bifurcated Grafts", Dep. Surgery Univ. Rochester, N. Y., U.S.A., 65$^{th}$ Scientific Sessions of the American Heart Association, New Orleans, 16–19 November, Vol. 86, No. 4, October, 1992] also reported on the successful use of digs to evaluate both straight and bifurcated grafts. Boudghene [F. Boudghene et al., "Endovascular Grafting in Elastase-induced Experimental Aortic Aneurysms In Dogs: Feasibility and Preliminary Results", *J. Vasc. Interv. Radiol.*, 4, (4), pp. 497–504, 1993] and co-workers described successful animal trials with endovascular grafting using elastase induced aortic aneurysms in the beagle dog. Later work conducted on the dog model and reported by Sayers et al. [R. D. Sayer et al., "Endovascular Repair of Abdominal Aortic Aneurysm: Limitations of the Single Proximal Stent Technique", *British Journal of Surgery*, 81, (8), pp. 1107–10, 1994] highlighted the need for both a proximal and distal stent for anchoring the graft. Using only a single stent resulted in back-bleeding around the distal end of the graft into the aneurysm sac.

As previously stated, the EVT device was the first to receive FDA surgical protocol approval for clinical evaluation. The first implant of the device was performed by W. S. Moore at the UCLA Medical Center on Feb. 10, 1993 [W. S. Moore, "The Role of Endovascular Grafting Technique in the Treatment of Infrarenal Abdominal Aortic Aneurysm", *Cardiovascular Surgery*, 3, (2), pp. 109–114, 1995]. Out of a screened population of 69 patients with AAA, ten were selected as suitable for endovascular repair. From these, eight were operated on using the EVT device and protocol and two required conversion to conventional aneurysm repair. None of the patients died as a result of the surgery, however, the long-term results for this new intervention are unknown. Moreover, as with all new techniques, randomized, prospective trials comparing standard therapy with endovascular grafting techniques will be needed [M. L. Martin, "Clinical Application of Endovascular Grafts in Aortoliac Occlusive Disease and Vascular Trauma", *Cardiovascular Surgery*, 3, (2), pp. 115–120, 1995].

Similar results were also obtained with the EVT device in Australia and reported in The Medical Journal of Australia by May et al. [J. May et al., "Endoluminal Repair of Abdominal Aortic Aneurysms", *The Medical Journal of Australia*, 161 (9), pp. 541–543, 1994]. Out of 12 patients selected as being suitable for endovascular repair with the EVT device, ten were successfully treated by the protocol whilst two cases were abandoned and treated by conventional open repair. After a mean follow-up period of seven months, no deaths were reported. More recent animal trial results using the EVT device were reported by W. J. Quinones-Baldrich et al. [W. J. Quinones-Baldrich et al., "Preliminary Experience with the Endovascular Technologies Bifurcated Endovascular Aortic Prosthesis in a Calf Model", *J. Vasc. Surg.*, 22, (4), pp. 370–379, 1995], the objective of the trial was primarily to evaluate a bifurcated endoluminal prosthesis for transfemoral placement in the aortoiliac position using the calf model as human simulation. Although successful deployment was regularly achieved where a neck of at least 12 mm in length was present, the calf model was found not suitable for chronic graft evaluation due to its sensitivity to spinal chord ischemia.

Successful results were achieved using the EVT device at the Leicester Royal Infirmary, England and reported by Nasim [A. Nasim, et al., "Endovascular Repair of Abdominal Aortic Aneurysms", *The Lancet*, Vol. 343, pp. 1230–1, May 14$^{th}$, 1994]. An 82-year-old woman with a 5 cm symptomless infrarenal AAA and suitably screened for the procedure was successfully treated and made an uneventful recovery. Yusuf et al. [Yusuf et al., "Transfemoral Endoluminal Repair of Abdominal Aortic Aneurysm with Bifurcated Graft", *The Lancet*, Vol. 344, pp. 650–1, September 3$^{rd}$, 1994] are also developing an endovascular technique for the treatment of AAA at the University of Nottingham. Once again, through careful screening of patients a high success rate was achieved without haemodynamic compromise or major complications. Their research is currently focused on fabricating thinner grafts and deploying stents in necks under 15 mm in length.

It has been estimated that in a quarter of all patients with stents, blood clots accumulate sometimes reblocking the arteries. Johnson & Johnson, who currently manufacture ±75% of the 350,000 stents implanted each year, as well as other major companies, are developing coatings for stents to reduce their thrombogenic properties [A. Coghlan, "Heart Attacks Are Given the Slip", *New Scientist*, Nov. 4$^{th}$, 1995]. Generally, stent coatings can be classified as prosthetic (either passive or active) or biological. Typical examples of passive coatings are those which increase the hydrophobicity, such as pyrolytic carbon and urethanes. Active coatings include those which incorporate drugs, such as low-molecular weight heparin, which are slowly released to inhibit thrombus formation. Lastly, biological coatings are represented by seeding of endothelial cells over the stent before deployment [J. C. Palmaz, "Intravascular Stents: Tissue-Stent Interactions and Design Considerations", *American Journal of Roentgenology*, 160, (3), pp. 613–8, 1993; N. Bonzon et al., "New Bioactivation Mode for Vascular Prostheses made of Dacron® Polyester", *Biomaterials*, 16, (10), pp. 747–751, 1995].

As previously highlighted, J. C. Parodi is generally regarded as the pioneer surgeon in the field of endovascular grafting. In his latest journal publication Parodi [J. C. Parodi, "Endovascular Repair of Abdominal Aortic Aneurysms and Other Arterial Lesions", *J. Vasc. Surg.*, 21, pp. 549–557, 1995] reports on the results of the endovascular repair of 50 abdominal aortic aneurysms or iliac aneurysms undertaken between September 1990 and April 1994. In forty of the fifty procedures Parodi reported success, even though some secondary treatment was required in six patients. Of the ten failures, four were attributed to early procedural deaths, one late procedural death, and five leaks.

The present invention provides a method and apparatus for effectively implanting a graft in a vessel of a patient.

SUMMARY OF THE INVENTION

The present invention pertains to an apparatus for implanting a graft into a vessel of a patient. The apparatus comprises a mechanical delivery mechanism for delivering the graft to a desired location inside the vessel and then withdrawing from the vessel. The apparatus also comprises an anchoring mechanism for anchoring the graft to the interior surface of the vessel from the inside of the vessel. The anchoring mechanism is connected to the delivery mechanism.

The present invention pertains to a method of implanting a graft in a vessel of a patient. The method comprises the steps of delivering a graft to a desired location inside the vessel with a delivery mechanism. Next, there is the step of piercing the vessel from the interior of the vessel with anchors connected to the graft from inside the vessel. Then, there is the step of anchoring the anchors in the vessel to hold the graft in the vessel by changing the shape of the anchors.

BRIEF DESCRIPTION OF THE DRAWINGS

In the accompanying drawings, the preferred embodiment of the invention and preferred methods of practicing the invention are illustrated in which.

DESCRIPTION OF THE PREFERRED EMBODIMENT

Referring now to the drawings wherein like reference numerals refer to similar or identical parts throughout the several views, and more specifically to FIGS. 1–6 thereof, there is shown an apparatus 10 for implanting a graft 12 into a vessel 14 of a patient. The apparatus 10 comprises a mechanical delivery mechanism 16 for delivering the graft 12 to a desired location inside the vessel 14 and then withdrawing from the vessel 14. The apparatus 10 also comprises an anchor mechanism 18 for anchoring the graft 12 to the interior surface 20 of the vessel 14 from the inside of the vessel 14. The anchor mechanism 18 is connected to the delivery mechanism 16.

Preferably, the anchor mechanism 18 is adapted to pierce through the graft 12 and the vessel 14 from the interior surface 20 of the vessel 14 and engage with the exterior surface 22 of the vessel 14 under the operation of the delivery mechanism 16. The anchor mechanism 18 preferably separates from the delivery mechanism 16 after the anchor mechanism 18 has engaged the exterior surface 22 of the vessel 14 and the delivery mechanism 16 is withdrawn.

The delivery mechanism 16 preferably includes an expansion mechanism 24 which expands inside the vessel 14 to cause the anchor mechanism 18 to pierce the vessel 14. Preferably, the delivery mechanism 16 includes a housing 26 which is positioned about the expansion mechanism 24 to protect the expansion mechanism 24 while it is inside the vessel 14. The delivery mechanism 16 preferably includes a first catheter mechanism 28 connected to the housing 26 for moving the housing 26 relative to the expansion mechanism 24. Preferably, the delivery mechanism 16 includes a second catheter mechanism 30 in which the first catheter mechanism 28 is disposed and a third catheter mechanism 32 in which the second catheter mechanism 30 is disposed and the first catheter mechanism 28 extends through the expansion mechanism 24.

The expansion mechanism 24 is preferably connected to the second and third catheter mechanisms. Preferably, the second and third catheter mechanisms each have an end which is adapted to be disposed in the vessel 14 and the relative movement of the second and third catheter ends to each other cause the expansion mechanism 24 to expand or contract.

The anchor mechanism 18 preferably includes a plurality of anchors 38. Preferably the expansion mechanism 24 comprises a plurality of portions, each portion comprising spoke sets 40. There are preferably twenty spoke sets 40, but there could be more or less spoke sets 40. The spoke sets 40 are about 1–2 millimeters apart about the second and third catheter mechanisms. Each spoke set 40 is moveably attached to an anchor 38. Each spoke set 40 is connected to the second and the third catheter mechanism such that as the second catheter end 34 moves toward the third catheter end 36 when they are in the vessel 14, the spoke sets 40 expand radially outward relative to the first catheter mechanism 28 causing the anchors 38 on the spoke sets 40 to pierce the vessel 14.

Figure 7:
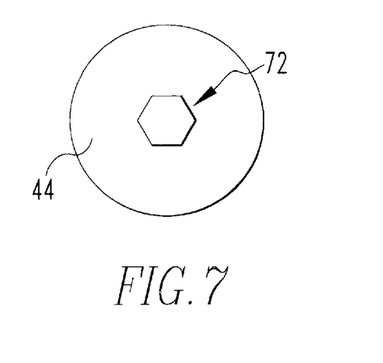
Figure 8:
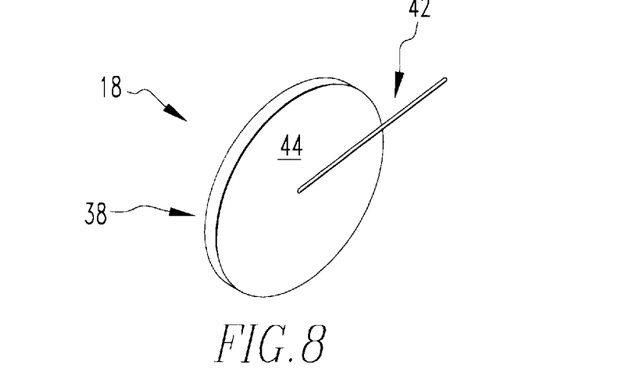
FIGS. 8 and 9 are schematic representations of the anchor with a nitinol pin having a first shape memory and a second shape memory, respectively.
Figure 9:
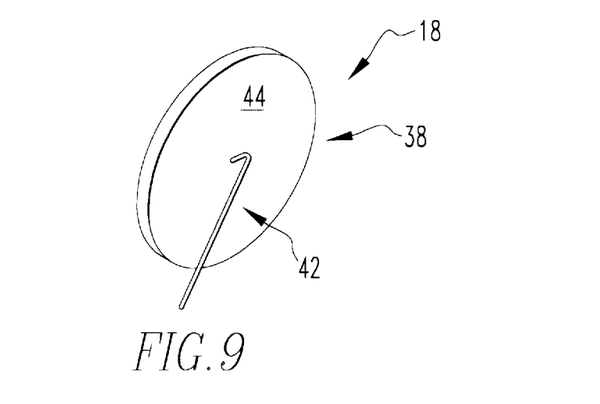

Preferably, at least a portion 42 of the anchor 38 is made of a material having a shape memory with a first memory shape being essentially of a straight pin, as shown in FIG. 8, to penetrate the vessel 14 and a second memory shape being essentially of a hooked pin, as shown in FIG. 9, which catches with the exterior surface 22 of the vessel 14. The anchor 38 preferably includes a base 44, as shown in FIG. 7, which removably attaches with the spoke set 40 and from which the material with memory shape extends.

Each spoke set 40 preferably includes an upper spoke 46 having a first upper end 48 and a second upper end 50 with the first upper end 48 hingedly connected to the second catheter end 34. Each spoke set 40 preferably also includes a first hinge 52 connected to the second upper end 50 of the upper spoke 46. Additionally, each spoke set 40 preferably includes a lower spoke 54 having a first lower end 56 and a second lower end 58 with the first lower end 56 hingedly connected to the third catheter end 36 and the first hinge 52 connected to the lower spoke 54 adjacent the second lower end 58 but with the second lower end 58 extending past the first hinge 52. The base 44 of the anchor 38 is engaged with the second lower end 58 such that when the third catheter end 36 moves toward the second catheter end 34, the upper and lower spokes pivot about the first hinge 52 and close upon each other as they move radially outward from the second and third catheter mechanisms and the anchor 38 on the second lower end 58 of the lower spoke 54 pierces the vessel 14. The upper and lower spokes retract back into a parallel position with the second catheter mechanism 30 as the third catheter end 36 moves away from the second catheter end 34.

Figure 10:
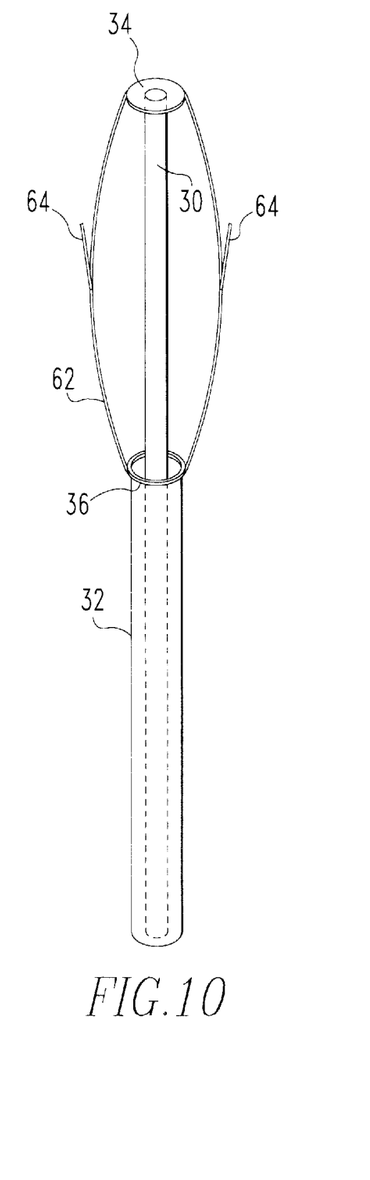
FIGS. 10 and 11 are schematic representations of a second embodiment of the present invention in different states of operation.
Figure 11:
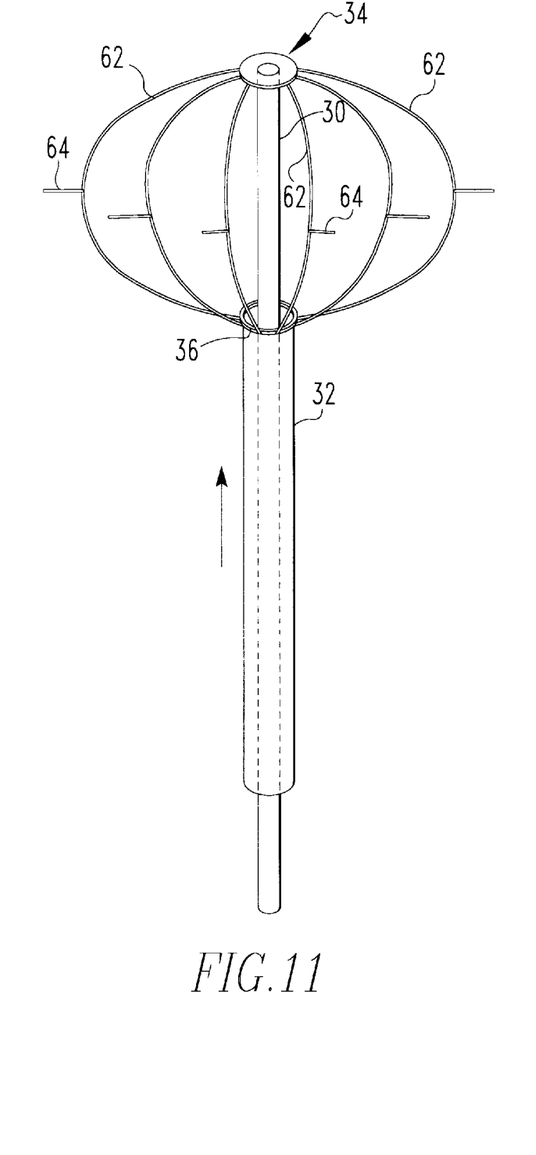
Figure 12:
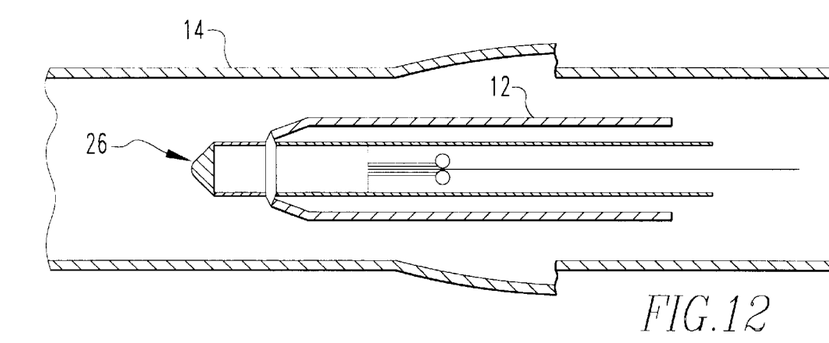
FIGS. 12—17 are schematic representations of a third embodiment of the present invention in different states of operation.
Figure 13:
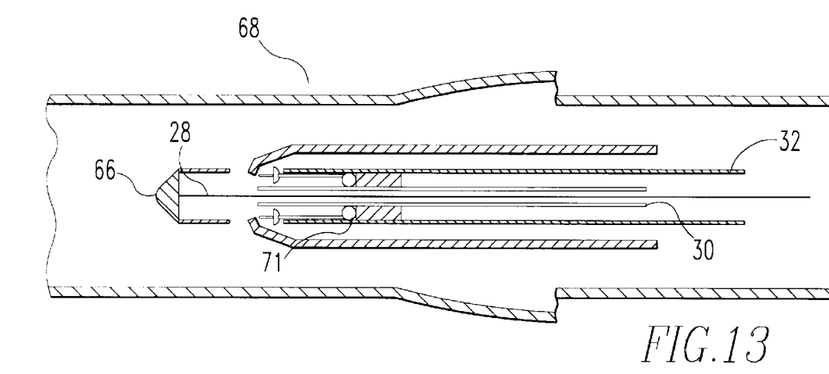
Figure 14:
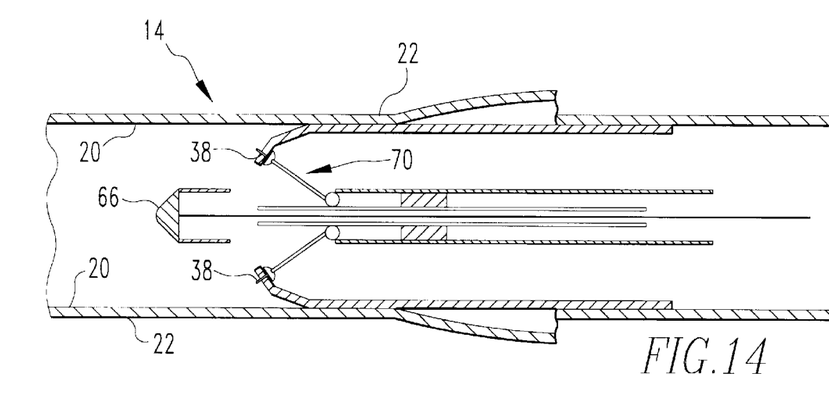
Figures 15, 15A:
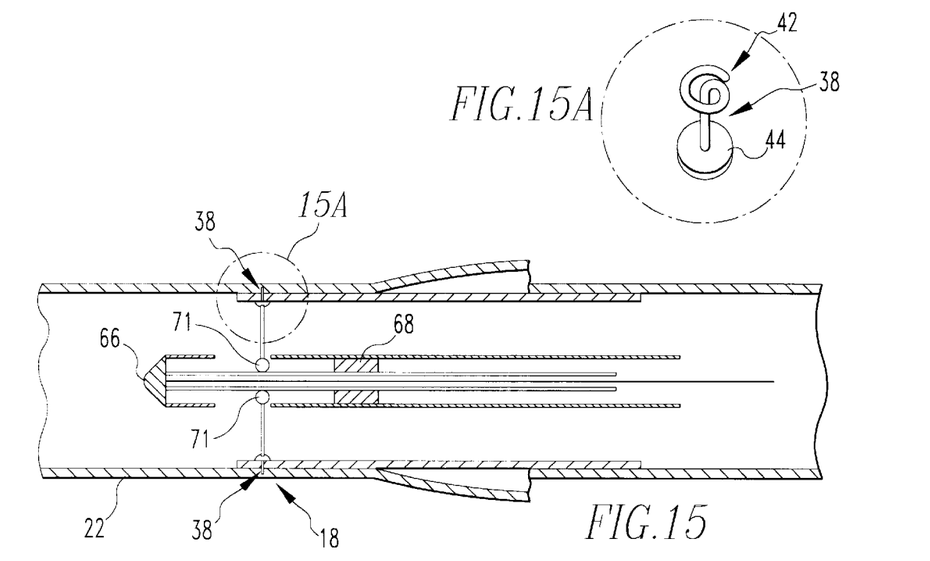
Figure 16:
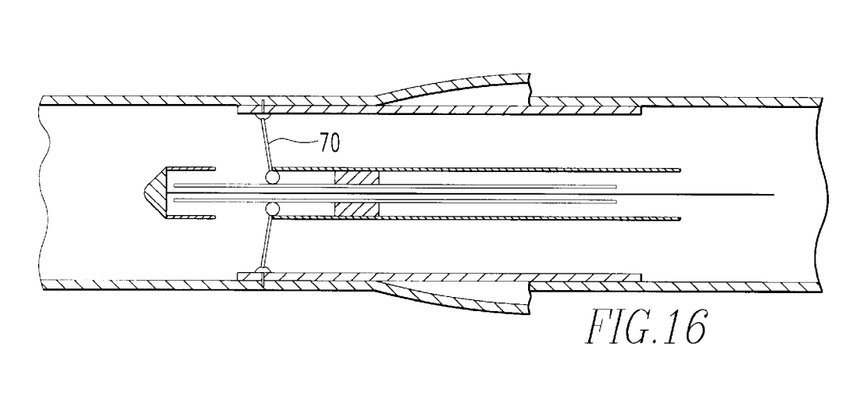
Figure 17:
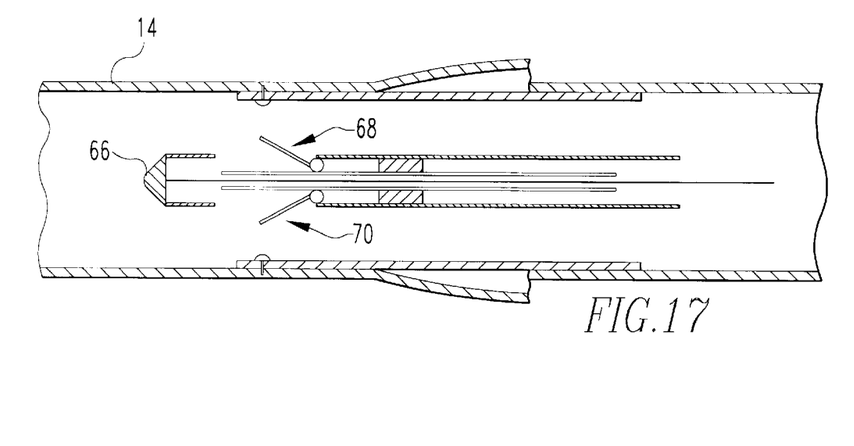
Figures 18A, 18B, 19, 20A, 20B:
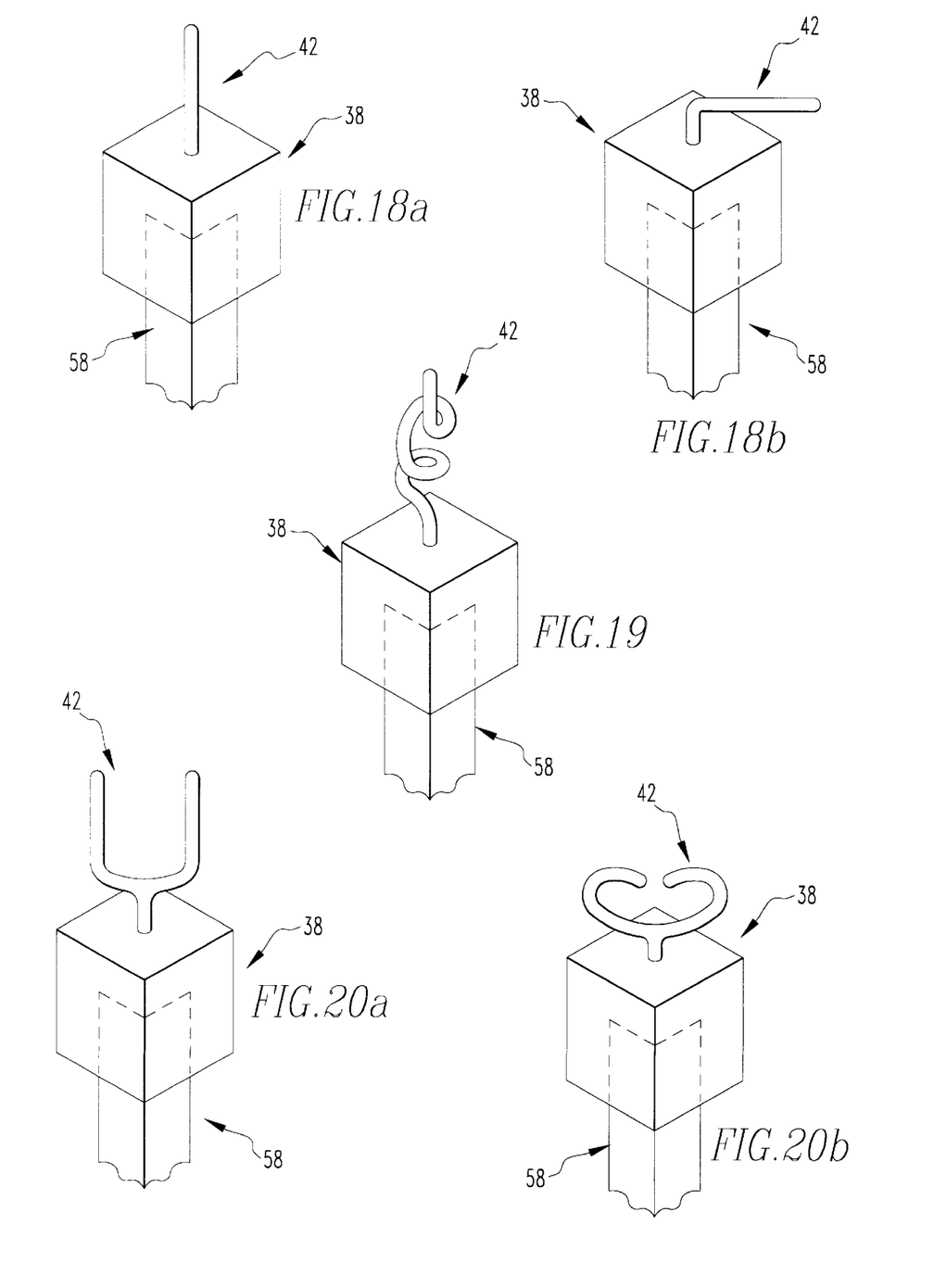
FIGS. 18a and 18b are schematic representations of an anchor in a first shape and a second shape, respectively. These drawings show the anchoring mechanism housed within the end of a spoke. The base of the anchoring mechanism is a hollowed out rectangular structure. Attached to the center of the top of this base is the straight nitinol pin. This pin is shown to deform either by bending or by twisting.
FIG. 19 is a schematic representation of another embodiment of an anchor.
FIGS. 20a and 20b are schematic representations of yet another embodiment of an anchor in a first shape and a second shape, respectively. These demonstrate an alternative shaped double pronged pin, which on deforming cause a staple-like effect.

Alternatively, as shown in FIGS. 10 and 11, the expansion mechanism 24 can include a mechanical balloon 60 connected to the second and third catheter mechanisms which extends outward from the second and third catheter mechanisms when the second and third catheter ends move toward each other and contracts inward toward the second and third catheter mechanisms when the second and third catheter ends move away from each other. Preferably, the anchor mechanism 18 includes a plurality of anchors 38, and the mechanical balloon 60 includes a plurality of bendable spokes 62 connected to the second and third catheter ends and disposed alongside each other about the circumference of the second and third catheter ends. Each bendable spoke 62 has a pin holder 64 made of memory shape material on which the anchor 38 is engaged. The pin holder 64 is connected to the center of the bendable spoke 62 such that when the second and third catheter ends move toward each other and the bendable spokes 62 bend outward from the second and third catheter mechanisms, the pin holder 64 extends perpendicularly from the bendable spoke 62 and the anchor 38 on the pin holder 64 pierces the vessel 14.

Alternatively, as shown in FIGS. 12-17, the housing 26 includes an upper housing 66 connected to the first catheter mechanism 28 and a lower housing 68 connected to the third catheter mechanism 32. The expansion mechanism 24 in such embodiment, can include a plurality of spring loaded spokes 70 each having an anchor 38 attached to them. The spring loaded spokes 70 each also have a spring 71. The spring 71 can be glued or welded to the second catheter mechanism 30 and the spring loaded spoke 70. Generally, in the various embodiments, the hinges can also be glued or welded in place. The spokes 70 are connected to the second catheter mechanism 30 adjacent the second catheter end 34 and about the circumference of the second catheter mechanism 30 such that when the spring loaded spokes 70 move away from the lower housing 26 and the second and third catheter ends move away from each other, they move open and extend perpendicularly from the second catheter mechanism 30 and force the anchors 38 attached to them to pierce the vessel 14.

The present invention pertains to a method of implanting a graft 12 in a vessel 14 of a patient. The method comprises the steps of delivering a graft 12 to a desired location inside the vessel 14 with a delivery mechanism 16. Next, there is the step of piercing the vessel 14 from the interior of the vessel 14 with anchors 38 connected to the graft 12 from inside the vessel 14. Then, there is the step of anchoring the anchors 38 in the vessel 14 to hold the graft 12 in the vessel 14 by changing the shape of the anchors.

Preferably, after the anchoring step, there is the step of withdrawing the delivery mechanism 16 from the vessel 14. Preferably, after the anchoring step there is also the step of separating the anchors 38 from the delivery mechanism 16.

The anchoring step preferably includes the step of anchoring the anchor 38 to the exterior surface 22 of the vessel 14. The piercing step preferably includes the step of expanding an expansion mechanism 24 of the delivery mechanism 16 which is adapted to expand inside the vessel 14 to cause the anchors 38 to pierce the vessel 14.

The delivery step preferably includes the step of moving a second catheter connected to the expansion mechanism 24 relative to a third catheter mechanism 32 connected to the expansion mechanism 24 to cause the expansion mechanism 24 to expand. The delivery step preferably also includes the step of moving a housing 26 with a first catheter mechanism connected to the housing 26 to expand the expansion mechanism 24.

In the operation of the preferred embodiment, the anchors 38 are first formed by inserting a portion of anchor portion 42, such as a straight pin which is made of shape memory alloy of nitinol, into a hexagonal hole 72 of the anchor base 44, as shown in FIG. 7. By inserting the nitinol pin into the hexagonal hole 72, the hexagonal shape prevents rotation or movement of the pin relative to the base 44. The nitinol pins of the anchors 38 are then inserted through the graft 12 to hold the graft 12 to them. Next, the base 44 of the anchors 38 are placed on the second lower end 58 of the lower spoke 54. The housing 26 is then placed over the upper spoke 46 and lower spoke 54 which form a spoke set 40. The upper spoke 26 and the lower spoke 54 are essentially in an unexpanded state and in parallel with the first catheter mechanism 28 which extends through the second catheter mechanism 30 and the third catheter mechanism 32 so the housing 26 can fit over them. The upper spoke 46 is connected to the second catheter end 34 at the first upper end 48 of the upper spoke 46. The lower spoke 54 is connected to the third catheter end 36 at the first lower end 56 of the lower spoke 54. The housing 26 with the first, second and third catheter mechanisms can be a Palmaz-Schatz Coronary Catheter System by Johnson & Johnson but could be modified according to the teachings herein to deliver a larger system. A femoral artery "cut down" open approach could be used for delivery.

When the patient is properly prepared, a guide wire 74 is inserted through a vascular sheath via a conventional femoral arteriotomy. The guide wire 74 is moved past the required anastomotic site in the patient, as is well known in the art. The housing with the pre-loaded graft 12 and the first, second and third catheter mechanisms, through which the guide wire 74 extend, are then fed up to the required anastomotic site along the guide wire 74, as is well known in the art.

Once the housing 26 with the pre-loaded graft 12 is in the desired position, the first catheter mechanism 28 is continued to the fed forward while the second and third catheter mechanisms are maintained still. This has the effect of separating the housing 26 from the spoke set 40 with the anchors 44 and the graft 12 so the spoke set 42 can be expanded. See FIGS. 1–5. The housing 26 serves to protect the vessel 14 through which the housing 26 is being moved and ultimately the aortic wall where the graft will ultimately be positioned from being scraped or cut from any exposed spokes anchors that may contact the wall during placement of the graft 12. In addition, to further enhance and facilitate exact positioning of the graft 12, a material can be injected to outline the artery via X Ray screening or other type of imaging techniques, as is well known in the art.

Figure 1:
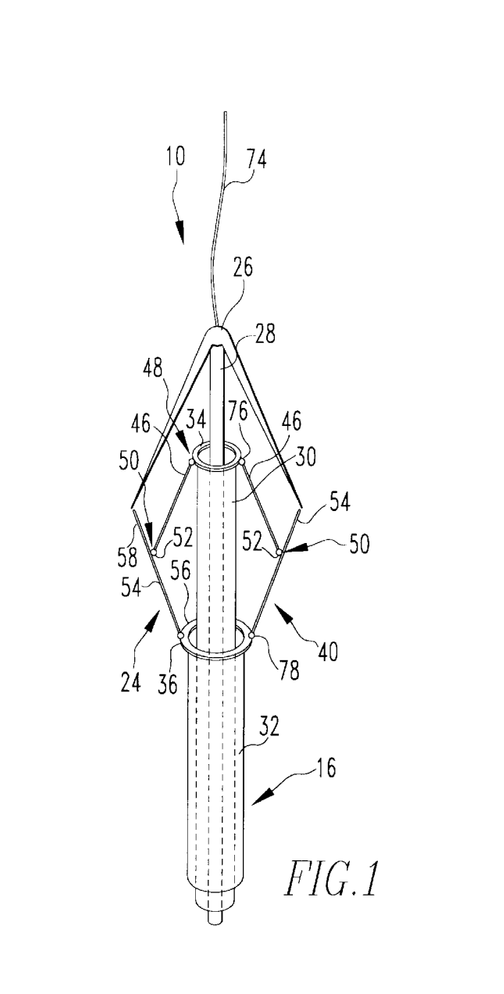
FIGS. 1–5 are schematic representations of a first embodiment of the present invention in different states of operation.
Figure 2:
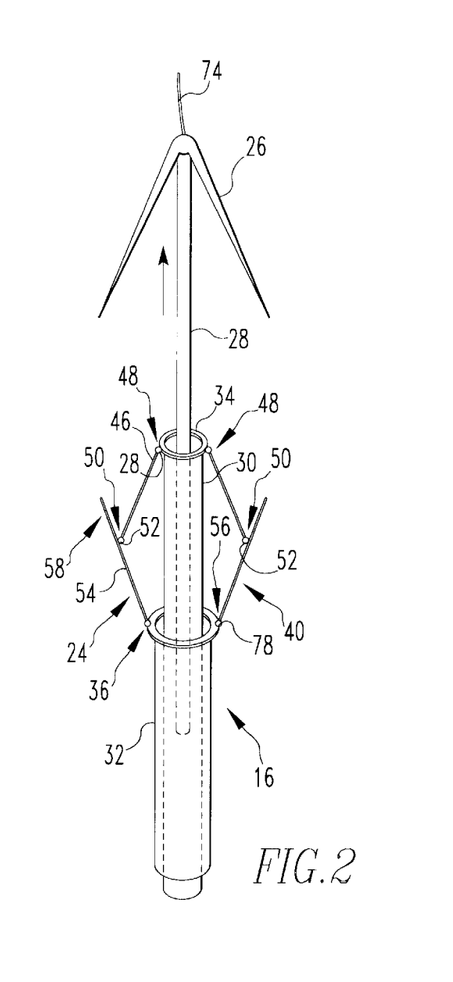
Figure 3:
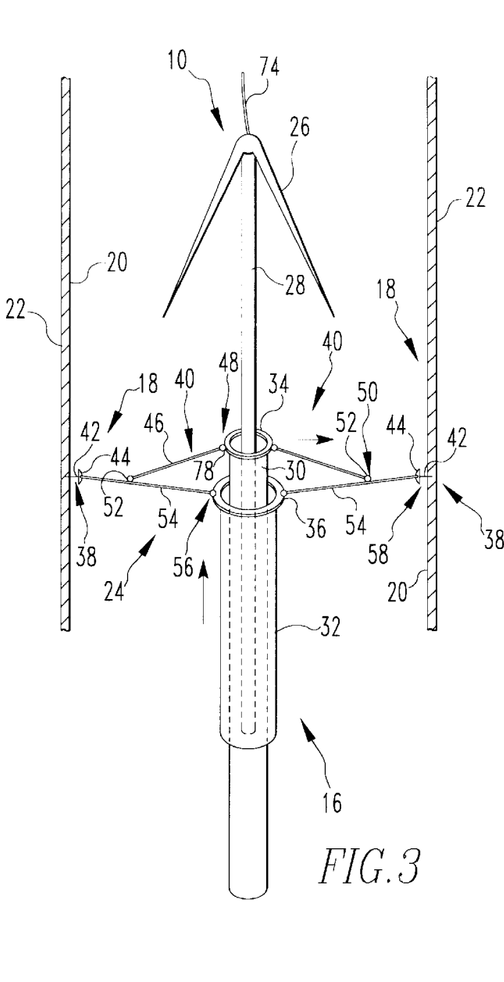

After the housing 26 has been moved out of the way, the third catheter mechanism is moved forward relative to the second catheter mechanism 28 so the third catheter end 36 moves closer to the second catheter end 34. The movement of the third catheter end 36 toward the second catheter end 34 has the effect of expanding outward the lower spoke 54 toward the vessel 14 so the lower spoke 54 extend essentially perpendicular with the third catheter mechanism 32. This happens because the first upper end 48 of the upper spoke 46 is connected through an upper hinge 76 to the second catheter end 34. Also, the second upper end 50 of the upper spoke is connected to the first hinge 52. In turn the lower spoke 54 is connected through its first lower end through a lower hinge 78 to the third catheter end 36. Adjacent to the second lower end 58 of the lower spoke 54 is attached the first hinge 54 but with the second lower end 58 extending past the first hinge 52. As the third catheter end 46 moves closer to the second catheter end 34, the lower spoke 54 and upper spoke 46 have only one direction to go because they are confined to rotation due to their hinge connections, and this direction is outward toward the vessel 14. The lower spoke 54 rotates outward about the lower hinge 78 due to the force of the upper spoke 46 against the lower spoke 54 because the upper spoke 46 cannot move away from the lower spoke 54 as the lower spoke 54 approaches it. However, because the upper spoke 46 is connected by the upper hinge 76 to the second catheter end, the upper spoke 46 rotates outward under the force of the lower spoke 54 moving closer to it, and also the first hinge allows the lower spoke 54 to continue to extend downward and rotate toward the vessel 14 as the third catheter end 46 moves closer to the second catheter end 34, as shown in FIGS. 2 and 3.

As the lower spokes 54 assume an essentially perpendicular relation with the third catheter mechanism 32, the graft 12 is dilated because the graft 12 is attached to the anchors 38 at the second lower end 58 of the lower spoke 54 which extends past the first hinge 52. As the second lower end 58 of the lower spoke 54 moves downward, it also moves with it the graft 12. At the same time the lower spokes 54 are forced outward from the third catheter mechanism 32 and the graft 12 is dilated, the portion 42 of the anchor 38 which extends beyond the base 44 and which pierces the graft 12, is forced through the aortic wall, first piercing the interior surface 20 and then piercing the exterior surface 22 of the vessel.

Once the nitinol pin has been forced through the aortic wall, after a specified time, the pin deforms so that it bends down laterally, forcing itself against the base 44 and piercing the external surface 42 of the aortic wall to better anchor the graft 12 to the aortic wall. The nitinol pin deforms naturally because of its memory shape attribute and can deform after about 15 minutes of being in position, as is well known in the art. Basically, the temperature of the patient's body is used to cause the nitinol pin to deform. It should be noted that there is plenty of space for blood flow to continue to pass through the aorta by passing around or passing through the spaces of the spokes and housing 26. Also, due to the lower spoke 54 extending with the force from the movement of the third catheter end 36, and the support of the upper spoke 46, the elasticity of the aortic wall and the subsequent aortic dilation is not enough to prevent the portion 42 of the anchor to pierce the aortic wall. Also, it is not necessary to predetermine the exact length of the lower spoke 54 for each aorta of each patient. The nitinol pins secure the graft to the vessel wall by deforming after penetrating and exiting the vessel wall. This is achieved by either bending causing a staple like effect or by twisting. Furthermore, more than one row of staples may be utilized to secure an adequate anastomosis.

After the anchors 38 are in place in the vessel 14 and have assumed their second memory shape, the third catheter mechanism 32 is moved down and away from the second catheter mechanism 30 so the third catheter end 36 moves away from the second catheter end 34. This has the effect of causing the lower spokes 54 to pull back from the anchors 38 through which the second lower end 58 is inserted in a slot 80 of the anchor 38 because as the third catheter end 36 moves away from the second catheter end 34, the upper spoke 46 to which the lower spoke 54 is connected through the first hinge does not move with the third catheter end 36. Instead, the second catheter end 34 stays still and as the third catheter end 36 moves away from the second catheter end 34, the upper spoke 46 by being connected to the lower spoke 54 through the first hinge 52 pulls the lower spoke 54 back in toward it. As the third catheter end 36 continues to move away, the upper spoke 46 is in turn pulled downward toward the second catheter mechanism 30, which further in turn pulls the lower spoke 54 further toward the second catheter mechanism 30. This action causes the upper and lower spokes to retract and also causes the second lower end 58 to slide out of the slot 80 of anchor 38.

Figure 4:
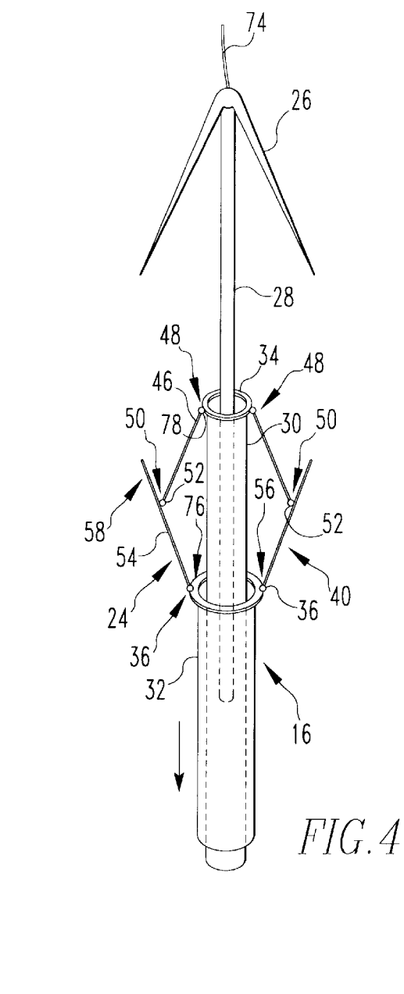
Figure 5:
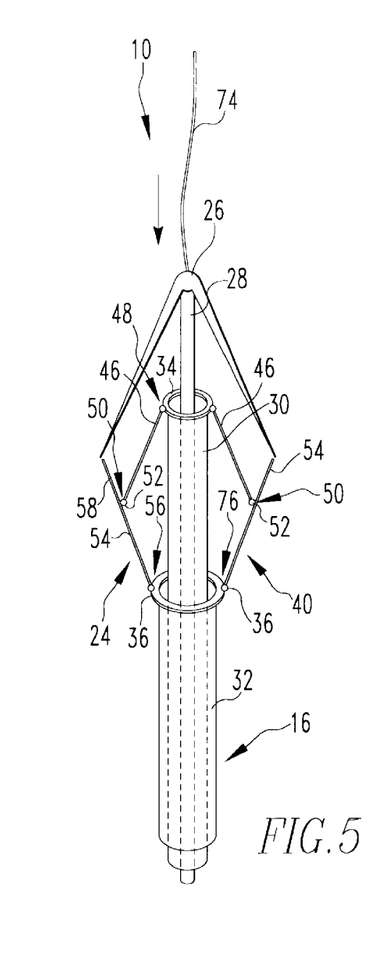
Figure 6:
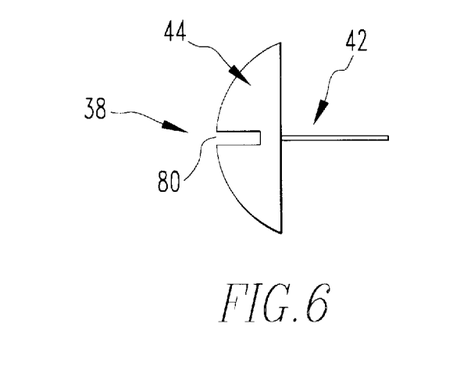
FIGS. 6 and 7 are schematic representations of a side view of an anchor and an overhead view of a base of an anchor, respectively.

When the upper and lower spokes 54 are fully retracted, the first catheter mechanism 38 is pulled downward relative to the second and third catheter mechanisms causing the housing to return over the upper and lower spokes. As shown in FIGS. 4 and 5. The second and third catheter mechanisms with the spoke sets 40 and the housing 26 is then removed from the patient as is well known in the art.

In regard to the alternative design of the mechanical balloon 60, as shown in FIGS. 10 and 11, it operates in very much the same way as the spoke set 40. However, instead of there being an upper and lower spoke forming a spoke set 40, there are one piece bendable spokes 62 connected to the second catheter end 34 and the third catheter end 36. The bendable spokes 62 bend outward as the third catheter end 36 moves closer to the second catheter end 34. Also, there is a pin holder 64 made of nitinol material which is connected to the center of the bendable spoke 62. After a period of time that the Nitinol pin holder 64 is exposed to the temperature of the patient, the pin holder 64 bends outward to take on essentially a perpendicular relation with the bendable spoke 62, which in turn causes the anchor to be positioned to penetrate the vessel 14. When the mechanical balloon 60 is expanded by the third catheter end 36 moving to the second catheter end 34, the anchors pierce the vessel 14 because the pin holders 64 move toward the vessel 14. The mechanical balloon 60 is contracted by the third catheter end 36 moving away from the second catheter end 34.

In another embodiment, as shown in FIGS. 12–17, instead of there being spoke sets 40 as described in the preferred operation of the preferred embodiment, there are spring loaded spokes 70 which are connected to the second catheter mechanism. The housing 26 includes an upper housing 66 and a lower housing 68. The spring loaded spokes 78 are maintained in the lower housing 68, which maintains them in a contracted state. After the upper housing 66 is separated from the lower housing 68, the second catheter mechanism 30 is moved relative to the third catheter mechanism 32 so the spring loaded spokes 70 move out of the lower housing 68. Since the spring loaded spokes 70 are pre-loaded to expand automatically once the constraint of the lower housing 68 is released, the spring loaded spokes 70 rotate outward to cause the spring loaded spokes 70 to extend perpendicularly from the second catheter mechanism 30. This action of the spring loaded spokes 70 forces the anchors 38 to penetrate the vessel 14. When it is time to retract the spring loaded spokes 70, the second catheter mechanism is pulled back relative to the third catheter mechanism, and the lower housing 68 pushes against the spring loaded spokes 70 as they are pulled back into the lower housing 68, causing the spring loaded spokes 72 to move back into a contracted state. There can be additional anchors at different locations of the graft if desired.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. An apparatus for implanting a graft into a vessel of a patient comprising:

a mechanical delivery mechanism for delivering the graft to a desired location inside the vessel and then withdrawing from the vessel, said delivery mechanism includes an expansion mechanism comprising a portion and a hinge about which the portion of the expansion mechanism rotates; and an anchoring mechanism for anchoring the graft to the interior surface of the vessel from the inside of the vessel, said anchoring mechanism connected to the delivery mechanism, said expansion mechanism expands inside the vessel to cause the anchoring mechanism to pierce the vessel, said anchoring mechanism is adapted to pierce through the graft and the vessel from the interior surface of the vessel and engage with the exterior surface of the vessel under the operation of the delivery mechanism.

2. An apparatus as described in claim 1 wherein the anchoring mechanism is adapted to separate from the delivery mechanism after the anchoring mechanism has engaged the exterior surface of the vessel and anchored in the vessel and the delivery mechanism is withdrawn.

3. An apparatus as described in claim 2 wherein the delivery mechanism includes a housing which is positioned about the expansion mechanism to protect the expansion mechanism while it is inside the vessel.

4. An apparatus as described in claim 3 wherein the delivery mechanism includes a first catheter mechanism connected to the housing for moving the housing relative to the expansion mechanism.

5. An apparatus is described in claim 4 wherein the delivery mechanism includes a second catheter mechanism in which the first catheter mechanism is disposed and a third catheter mechanism in which the second catheter mechanism is disposed and the first catheter mechanism extends through the expansion mechanism.

6. An apparatus as described in claim 5 wherein the expansion mechanism is connected to the second and third catheter mechanisms, said second and third catheter mechanisms each having an end which is adapted to be disposed in the vessel, and the relative movement of the second and third catheter ends to each other cause the expansion mechanism to expand or contract.

7. An apparatus as described in claim 6 wherein the anchoring mechanism includes a plurality of anchors, and wherein the expansion mechanism comprises a plurality of portions, each portion comprising a spoke set, each spoke set moveably attached to an anchor, each spoke set connected to the second and the third catheter mechanisms such that as the second catheter end moves toward the third catheter end when they are in the vessel, the spoke sets expand radially outward relative to the first catheter mechanism causing the anchors on the spoke sets to pierce the vessel.

8. An apparatus as described in claim 7 wherein at least a portion of the anchor is made of a material having a shape memory with a first memory shape being essentially of a straight pin to penetrate the vessel and a second memory shape being essentially of a hooked pin which catches with the exterior surface of the vessel.

9. An apparatus as described in claim 8 wherein the anchor includes a base which removably attaches with the spoke set and from which the material with memory shape extends.

10. An apparatus as described in claim 9 wherein each spoke set includes an upper spoke having a first upper end and a second upper end with said first upper end hingedly connected to the second catheter end, a first hinge connected to the second upper end of the upper spoke; and a lower spoke having a first lower end and a second lower end with the first lower end hingedly connected to the third catheter end and the first hinge connected to the lower spoke adjacent the second lower end but with said second lower end extending past said first hinge, said base of said anchor engaged with said second lower end such that when the third catheter end moves toward the second catheter end, the upper and lower spokes pivot about the first hinge and close upon each other as they move radially outward from the second and third catheter mechanisms and the anchor on the second lower end of the lower spoke pierces the vessel, said upper and lower spokes retracting back into a parallel position with the second catheter mechanism as the third catheter end moves away from the second catheter end.

11. An apparatus as described in claim 6 wherein the expansion mechanism comprises a mechanical balloon connected to the second and third catheter mechanisms which extends outward from the second and third catheter mechanisms when the second and third catheter ends move toward each other and contracts inward toward the second and third catheter mechanisms when the second and third catheter ends move away from each other.

12. An apparatus as described in claim 11 wherein said anchor mechanism includes a plurality of anchors, and the mechanical balloon includes a plurality of bendable spokes connected to the second and third catheter ends and disposed alongside each other about the circumference of the second and third catheter ends, each bendable spoke having a pin holder made of memory shape material on which the anchor is engaged, said pin holder connected to the center of the bendable spoke such that when the second and third catheter ends move toward each other and the bendable spokes bend outwards from the second and third catheter mechanisms, the pin holder extends perpendicularly from the bendable spoke and the anchor on the pin holder pierces the vessel.

13. An apparatus as described in claim 6 wherein the housing includes an upper housing connected to the first catheter mechanism and a lower housing connected to the third catheter mechanism and wherein the expansion mechanism includes a plurality of spring loaded spokes each having an anchor attached to them, said spring loaded spokes each also having a spring, said spokes connected to the second catheter mechanism adjacent the second catheter end and about the circumference of the second catheter mechanism such that when the spring loaded spokes move away from the lower housing and the second and third catheter ends move away from each other, they move open and extend perpendicularly from the second catheter mechanism and force the anchors attached to them to pierce the vessel.

14. A method of implanting a graft in a vessel of a patient comprising the steps of:

delivering a graft to a desired location inside the vessel with a delivery mechanism;

expanding an expansion mechanism of the delivery mechanism about a hinge of the expansion mechanism;

piercing the vessel from the interior of the vessel with anchors connected to the graft from inside the vessel from the action of the expansion mechanism; and anchoring the anchors in the vessel to hold the graft in the vessel by changing the shape of the anchors.

15. A method as described in claim 14 including after the anchoring step, there is the step of withdrawing the delivery mechanism from the vessel.

16. A method as described in claim 15 wherein the anchoring step includes the step of anchoring the anchor to the exterior surface of the vessel.

17. A method as described in claim 16 including after the anchoring step, there is the step of separating the anchors from the delivery mechanism.

18. A method as described in claim 17 wherein the piercing step includes the step of expanding an expansion mechanism of the delivery mechanism which is adapted to expand inside the vessel to cause the anchors to pierce the vessel.

19. A method as described in claim 18 wherein the delivery step includes the step of moving a second catheter connected to the expansion mechanism relative to a third catheter mechanism connected to the expansion mechanism to cause the expansion mechanism to expand.

20. An apparatus for implanting a graft into a vessel of a patient comprising:

a mechanical delivery mechanism for delivering the graft to a desired location inside the vessel and then withdrawing from the vessel, the delivery mechanism includes an expansion mechanism, the delivery mechanism includes a housing which is positioned about the expansion mechanism to protect the expansion mechanism while it is inside the vessel, the delivery mechanism includes a first catheter mechanism connected to the housing for moving the housing relative to the expansion mechanism, the delivery mechanism includes a second catheter mechanism in which the first catheter mechanism is disposed and a third catheter mechanism in which the second catheter mechanism is disposed and the first catheter mechanism extends through the expansion mechanism, the expansion mechanism is connected to the second and third catheter mechanisms, said second and third catheter mechanisms each having an end which is adapted to be disposed in the vessel, and the relative movement of the second and third catheter ends to each other cause the expansion mechanism to expand or contract; and an anchoring mechanism for anchoring the graft to the interior surface of the vessel from the inside of the vessel, said anchoring mechanism connected to the delivery mechanism, said anchoring mechanism is adapted to pierce through the graft and the vessel from the interior surface of the vessel and engage with the exterior surface of the vessel under the operation of the delivery mechanism, the anchoring mechanism is adapted to separate from the delivery mechanism after the anchoring mechanism has engaged the exterior surface of the vessel and anchored in the vessel and the delivery mechanism is withdrawn, said expansion mechanism expands inside the vessel to cause the anchoring mechanism to pierce the vessel.

21. A method of implanting a graft in a vessel of a patient comprising the steps of:

delivering a graft to a desired location inside the vessel with a delivery mechanism;

piercing the vessel from the interior of the vessel with anchors connected to the graft from inside the vessel;

anchoring the anchors in the exterior surface of the vessel to hold the graft in the vessel by changing the shape of the anchors; and withdrawing the delivery mechanism from the vessel.

\* \* \* \* \*